(12) United States Patent
Hoogewind

(10) Patent No.: US 6,260,197 B1
(45) Date of Patent: Jul. 17, 2001

(54) WELDING HELMET WITH CONICAL PIVOTING MECHANISM FOR HEAD GEAR STRAP

(75) Inventor: Todd Richard Hoogewind, Grand Rapids, MI (US)

(73) Assignee: Jackson Products, Inc., Chesterfield, MO (US)

( * ) Notice: Subject to any disclaimer, the term of this patent is extended or adjusted under 35 U.S.C. 154(b) by 0 days.

(21) Appl. No.: 09/288,875

(22) Filed: Apr. 9, 1999

(51) Int. Cl.$^7$ .................................................... A61F 9/06
(52) U.S. Cl. ...................................... 2/8; 403/408.1
(58) Field of Search ........................... 2/8, 9; 403/408.1, 403/116, 117, 334

(56) References Cited

U.S. PATENT DOCUMENTS

| | | | |
|---|---|---|---|
| 2,360,101 | * 10/1944 | Bowers | 2/8 |
| 3,074,072 | * 1/1963 | Edwards et al. | 2/8 |
| 3,075,201 | * 1/1963 | Linblom | 2/8 |
| 3,430,263 | * 3/1969 | Newcomb | 2/8 |
| 4,464,800 | * 8/1984 | Edwards | 2/8 |
| 5,141,357 | * 8/1992 | Sherman et al. | 403/408.1 |
| 5,713,688 | * 2/1998 | McCallum | 403/57 |
| 6,010,274 | * 1/2000 | Abouzahr | 403/408.1 |

* cited by examiner

Primary Examiner—Michael A. Neas
(74) Attorney, Agent, or Firm—Dunlap, Codding & Rodgers, P.C.

(57) ABSTRACT

A welding helmet includes a connector for connecting the head gear and the protective shell and is comprised of an external finger knob allowing for user adjustment of the friction developed by the connector, a conical pivot stop having a conical surface, a strap member having a matching conical surface with the frictional forces being developed between these two conical surfaces, and a bolt which joins the parts of the connector and mounts them between the head gear and shell. A guide pin and guide slot in the stop and strap member control and guide the movement between these two parts as the shell is moved with respect to the user's head. A locator pin in the stop is inserted into one of a series of holes in the helmet to locate the angular orientation between the stop and the helmet, and thereby helps to fix the limits of relative movement between the shell and the user's head.

20 Claims, 2 Drawing Sheets

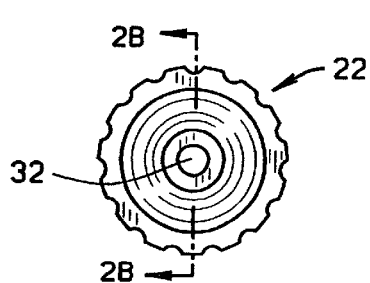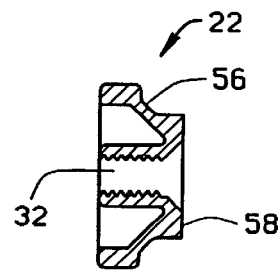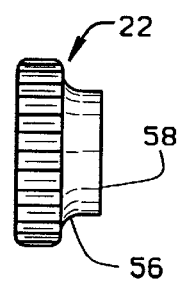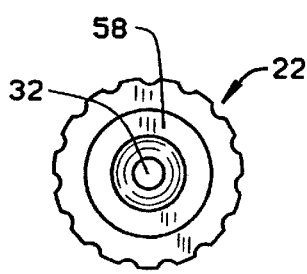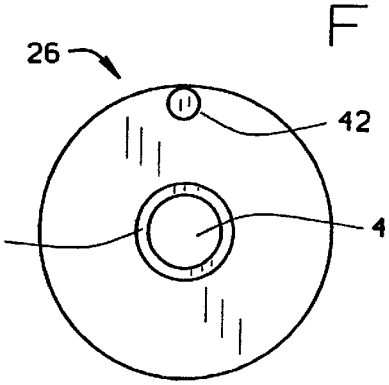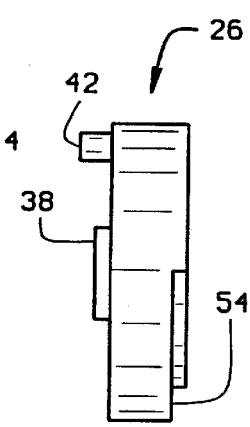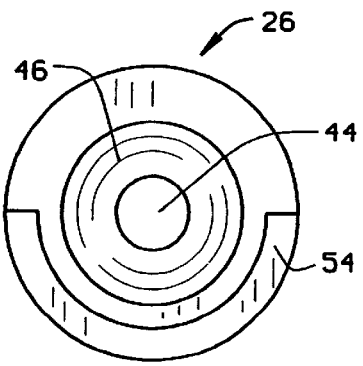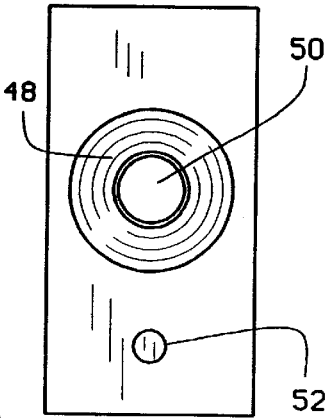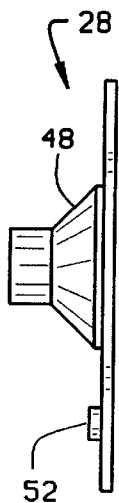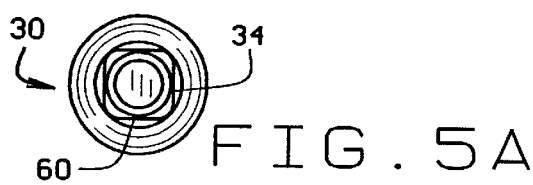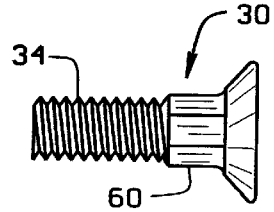

WELDING HELMET WITH CONICAL PIVOTING MECHANISM FOR HEAD GEAR STRAP

BACKGROUND OF THE INVENTION

Welding and other protective helmets and head gear are well known in the prior art. These helmets are generally worn on the head of the user and protect his head, face and eyes. They typically include a hard protective shell which covers the users head in some manner and a support strap of some kind that fastens to the protective shell and mounts it to the user's head. For comfort and a secure fit, there is usually provided some kind of adjustment not only in the head gear strap itself but also in the point of attachment between the protective shell and the head gear. However, this point of attachment is generally not seriously considered as a likely place to provide any significant adjustment not only for cost reasons, but also because the head gear strap is itself typically adjustable. In the welding helmet application in particular, this connection point between the shell and the head gear is perhaps more important as a welder will typically "nod" his helmet up and out of the way, or down in protective position, with a sharp sudden movement of his head. With this "nodding" movement, the connection point provides a point of pivot for the protective shell which is independent of any head gear adjustment. Thus, at least for welding helmets, or for any protective helmet for which this "nodding" motion is used, the pivot point at the connection has increased importance. Another aspect to this "nodding" motion is that continuous movement will have a tendency to loosen the pivot point, as the shell can be not insubstantially light and generate a torque as it is "nodded". Additionally, the welding helmet may vary in weight as the user adds, deletes, or changes filters or otherwise modifies his helmet configuration. Thus, a proper "nodding" movement will not be achieved should the weight of the shell be changed. Therefore, it would be desirable to provide a pivot connection that allows the user to readily adjust the frictional engagement between the shell and the head gear to accommodate such changes in weight.

This pivot point connection is also the point where the range of movement for the shell needs to be controlled in order that when "nodded", the shell moves between a desired up position and a desired down position. Obviously, for different users, these end or stopped positions will vary due to their anatomical differences. Furthermore, it is important that these end or stopped positions be somewhat reliably set, and maintained, as a welder could be less than attentive and assume that the shell will move to where he thought it was adjusted and should the shell slip or otherwise not fully move to the proper position, he could find himself welding or at least striking an arc with the helmet not in its full protective position. Injury could occur should the welder be careless in this manner. Therefore, incorporating this mechanical stop into a pivot connection can be important to a safe and idiot proof operation of the helmet.

In the prior art, this connection point was not focussed on and many welding helmets have simple screw fasteners which tighten down on the shell itself, using the simple annular area of a bolt or accompanying washer as the surface against which the frictional forces are developed. These are found to routinely work themselves loose through repeated use. Or, complicated structure has been used in other prior art designs which are an improvement over the simple screw down fasteners, but they can suffer from increased cost and still not provide the additional surface area thought to be needed to develop a workable frictional force that provides safer and more reliable operation.

In order to solve these and other problems in the prior art, the inventor herein has succeeded in designing and developing a pivot connection that is elegantly simple, with a minimum number of parts and hence inexpensive, which provides a greatly increased surface area for developing a significantly greater frictional force and which at the same time is infinitely adjustable by the user with a simple finger sized twist knob. This same elegantly simple design further provides two mechanical stops for a user to adjust the limit of movement of the helmet during the "nodding" motion. One of these mechanical stops is user adjustable with the parts provided to set the end points of the movement, and the other is adjustable by changing out a single piece of the assembly. Together they determine the end points of the "nodding" motion and also provide a mechanical track along which the parts are guided as they move to better control the movement. Essentially, these parts include an outside finger adjust knob with a threaded hole, a conical pivot stop having a conical surface and a pin for insertion in one of a number of matching holes in the helmet interior to fix its angular orientation, the conical pivot stop having a conical surface with a central hole, a strap member for attachment to the head gear with the strap member including a matching conical surface with central hole, and a fastening bolt for insertion through all of the parts and threading into the finger adjust knob. Thus, these few parts provide the pivot connection between the helmet shell and the head gear, a conical surface against which a significantly increased frictional force is developed dependent on the user's tightening of the finger knob, and a mechanical stop which adjustably fixes the end points of motion and which tracks the parts to better control their movement and ensure that they move smoothly and accurately. The parts may be made of any convenient material such as high impact plastic or other materials which will hold up under the conditions of use. These parts can be made with high speed production equipment and can be assembled readily without specific adjustment required at the factory. The parts are thus low cost, and while some Limited assembly is required, the invention provides increased functionality at Lower cost than those pivot connections of the prior art.

While the principal advantages and features of the invention have been explained, a fuller understanding of the invention may be attained by referring to the drawings and description of the preferred embodiment which follows.

BRIEF DESCRIPTION OF THE DRAWINGS

FIGS. 2a–2d depict various views of the finger knob;

FIGS. 3a–3c depict various views of the conical pivot stop;

FIGS. 4a–4b depict various views of the strap member; and

FIGS. 5a and 5b depict various views of the bolt which secures the parts of the pivot connection together and to the helmet.

DETAILED DESCRIPTION OF THE PREFERRED EMBODIMENT

Figure 1:
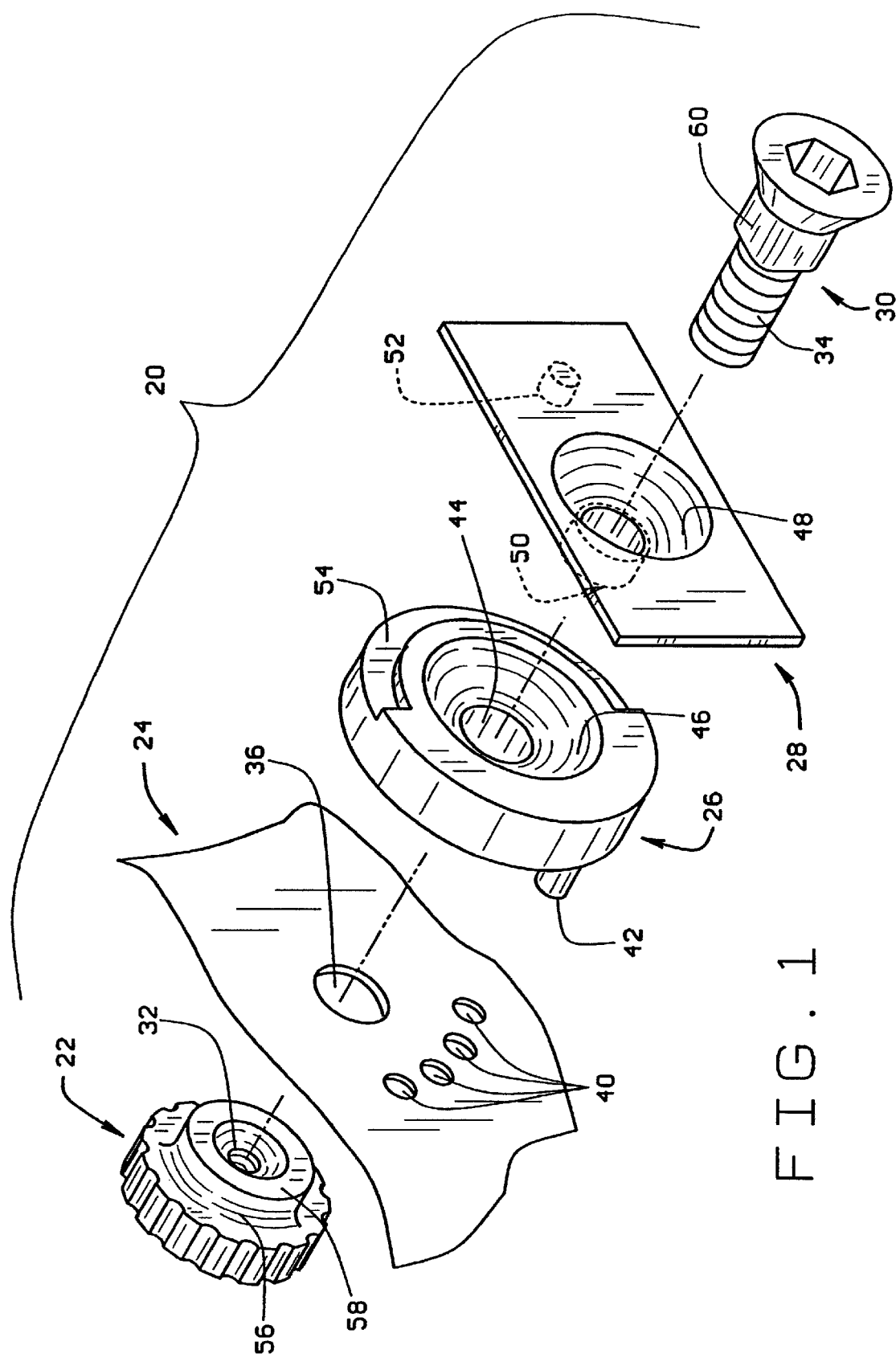
FIG. 1 is an exploded view of the pivot connection of the present invention also showing it's orientation with respect to the protective shell.

As shown in FIG. 1, the pivot connection 20 of the present invention includes a finger knob 22 which is positioned outside the helmet shell 24, a conical pivot stop 26 which fits into the helmet 24, a strap member 28 which is secured to the head gear, and a bolt 30 which fits through each of the foregoing to secure them together and to the helmet 24. While each of these parts will be explained in more detail below, it is perhaps helpful to explain how they are assembled and fit to each other in order that the detailed description will be better understood.

Starting with the knob 22, it is noted that the knob 22 has a threaded opening 32 which receives the threaded end 34 of the bolt 30 to fasten all of the parts together and to the helmet 24. The helmet 24 includes a central opening 30 which receives a shoulder 38 (see FIG. 3) of the conical pivot stop 26 and a series of smaller holes 40 which receive a locator pin 42 of the conical pivot stop 26 so that it is located both radially and circumferentially with respect to the helmet 24. The locator pin 42 fixes the "down" position of the helmet 24 with respect to the user's face, and also fixes the location of the guide slot 54 as explained below. The conical pivot stop 26 also has a center hole 44 through which the bolt 30 fits, and a conical surface 46 for receiving a matching conical projection 48 on the strap member 28. It is between these two matching conical surfaces 46, 48 that the frictional force is developed. The strap member 28 is secured to the head gear and also has a center hole 50 (see FIG. 4). A guide pin 52 on the strap member 28 is received by an arcuately shaped guide slot 54 in the conical pivot stop 26 to guide the movement between the head gear and the helmet 24 as the pivot connection 20 operates. The ends of the guide slot 54 determine the extent of permitted movement between the conical pivot stop 26 and the strap member 28, thereby determining the limits of movement between the helmet 24 and the head gear. Lastly, the bolt 30 fits through each of the aforementioned parts and fastens them together and to the helmet 24.

In operation, once assembled, the user need merely twist the finger knob, which is outside the helmet, in order to adjust the amount of friction generated between the two conical surfaces and thereby control the ease with which the helmet can be moved with a "nodding" motion. It could be adjusted to permit free fall, i.e. very little friction, or movement upon a concerted "nod", i.e. perhaps medium friction, or movement only with hand contact, i.e. perhaps strong friction, or no movement at all, i.e. lockup. Should the user desire to change the range of permitted motion, he need only loosen the finger knob to permit the conical pivot stop 26 to be moved away from the helmet 24 and disengage the locating pin 42 from the particular hole 40 it was in and to insert it into another hole 40, as desired. Still another adjustment of the degree of movement could be effected with a change out of the conical pivot stop 26 to another having a different arcuate guide slot 54, i.e. located at another arcuate position or having a different length.

The individual parts comprising the pivot connection 20 of the present invention are shown in FIG. 2–5, and will now be described. The finger knob 22 is shown in FIG. 2a–d and includes a knurled periphery for a user to grip the knob 22, a central threaded bore 32 to receive the threaded bolt end 34, and an angled annular transition 56 therebetween. An inner shoulder 58 provides a relatively large contact surface against which the helmet 24 and the conical pivot stop shoulder 38 rests.

The conical pivot stop 26 is shown in FIG. 3a–c and depicts the shoulder 38, the central hole 44, the conical surface 46, the locator pin 42, and the guide slot 54. The particular incline angle for the cone shaped conical surface 46 is a matter of design choice and is not considered to be of critical importance. It is only important that a much larger surface be provided against which the frictional forces may be developed to provide increased user control, a smoother action, and more secure attachment between the parts. The shoulder 38 is sized to fit within and locate the stop 26 in helmet hole 36. The guide slot 54 is shown to extend a full 180 degrees. However, the angular extent of the guide slot 54 is also, to a certain extent, a matter of design choice. The slot 54 should extend far enough to allow the helmet to move between a full up and down position on a typical user. The locator pin 42 is shown directly opposite the slot 54. Again, its location with respect to the slot 54 is a matter of design choice and some adjustment of its relative position is possible through the series of holes 40 in the helmet 24. To provide even greater adjustment for the user, a different stop 26 may be changed out which has a different angular orientation between the locator pin 42 and the slot 54. In other words, the stop 26 may have its slot 54 in a different relative position to the pin 42 than shown in FIG. 3.

The strap member 28 is shown in FIG. 4a–b and depicts the guide pin 52 which fits slideably in guide slot 54 and which serves to guide the movement of the parts as the "nodding" movement is achieved. This adds stability to the assembly and helmet. An alternative design is also shown in FIG. 4b showing the feature of a threaded stem 58 as part of the strap member 28 which takes the place of a separate bolt 30. If this alternate design is not used, the strap member 28 is merely truncated and has a continuous conical surface 48 terminating into the central hole 50. Also, the matching conical surface 48 is shown that is brought into contact with the conical surface 46 of stop 26.

The bolt 30 is shown in FIG. 5a–b and has a threaded end 34, a shank 60 which fits within and can be used as a bearing for the stop 26 and strap member 28 as they rotate with respect to each other, and a tapered head which allows the bolt 30 to be snugged up against the conical surface 48 without damaging it.

While the inventor has disclosed his invention in the form of the preferred embodiment, it would apparent to one of ordinary skill in the art that various changes and modifications could be made without departing from the spirit and scope of the invention. Some of these have been specifically pointed out but others could be thought of that fit within the inventor's teaching. Accordingly, the invention should be limited only by the scope of the claims and their equivalents.

What is claimed is:

1. A welding helmet comprising a shell and a head strap for supporting the shell from a wearer's head, and at least one connection between said head strap and the shell to thereby secure the two together, said connection including a friction bearing between said shell and said head strap and being user adjustable to thereby control the amount of friction applied between said shell and head strap, the connection further including a mechanical stop for defining the limits to the range of motion available between the shell and strap, the mechanical stop comprising a pin and receiving slot, said pin fitting into said slot and limiting the range of movement of said pin to thereby limit the range of pivot between said strap and shell, the mechanical stop further comprising a second pin and a plurality of holes into any one of which said second pin is fitted to fix end points in the range of motion permitted by said connection.

2. The welding helmet of claim 1 wherein said friction bearing includes a substantially conical fitting comprised of a first member secured to said strap and a mating second member secured to said shell.

3. The welding helmet of claim 2 wherein said first member comprises a conical projection having a central hole for receiving a fastener, and the second member comprises a conical pivot stop having a central hole for matching and lining up with the first member's hole so that the fastener may fit through both holes and secure the first and second members together.

4. The welding helmet of claim 3 wherein said fastener comprises a through bolt and a knob, said bolt and knob securing said connection to said shell and strap.

5. A welding helmet comprising a shell and a head strap for supporting the shell from a wearer's head, and at least one connection between said head strap and the shell to thereby secure the two together, said connection including a friction bearing between said shell and said head strap and being user adjustable to thereby control the amount of friction applied between said shell and head strap, said friction bearing including a substantially conical fitting comprised of a first member secured to said strap and a mating second member secured to said shell, the connection further comprising a mechanical stop for defining the limits to the range of motion available between the shell and strap.

6. The welding helmet of claim 5 wherein said mechanical stop comprises a mechanical linkage interconnecting the first member and the second member of the conical fitting of said connection, and wherein said connection further comprises a pin and a mating plurality of holes into one of which said pin fits in order to fix the limits on the range of motion of said mechanical linkage.

7. The welding helmet of claim 6 wherein two of said connections secure said strap to said shell.

8. A connector for a welding helmet to secure a head gear to said welding helmet, said connector comprising a conical pivot stop having a first substantially conical surface, a strap member having a second, mating substantially conical surface, a mechanical stop for defining the limits to the range of motion available between the helmet and head gear, and a fastener for securing said conical pivot stop and said strap member to said head gear and helmet so that said first and second substantially conical surfaces are brought into engagement as said connector is assembled, adjustment of said fastener adjusting the friction between said first and second members to thereby adjust the ease of pivoting movement between said helmet and said head gear.

9. The connector of claim 8 wherein said mechanical stop comprises a mechanical linkage interconnecting the conical pivot stop and the strap member of said connector, and wherein said connector further comprises a pin adapted to fit into one of a mating plurality of holes in said helmet in order to fix the limits on the range of motion of said mechanical linkage.

10. The connector of claim 9 wherein said mechanical linkage comprises a protrusion and slot, one of said protrusion and slot being located on said conical pivot stop and the other of said protrusion and slot being located on said strap member.

11. A welding helmet has a connector to secure a head gear to said welding helmet, said connector comprising a conical pivot stop having a first substantially conical surface, a strap member having a second, mating substantially conical surface, a mechanical stop for defining the limits to the range of motion available between the helmet and head gear and a fastener for securing said conical pivot stop and said strap member to said head gear and helmet so that said first and second substantially conical surfaces are brought into engagement as said connector is assembled, adjustment of said fastener also adjusts the friction between said first and second members to thereby adjust the ease of pivoting movement between said helmet and said head gear.

12. The welding helmet of claim 11 wherein said mechanical stop comprises a mechanical linkage interconnecting the conical pivot stop and the strap member of said connector, and wherein the connector further comprises a pin adapted to fit into one of a mating plurality of holes in said helmet in order to fix the limits on the range of motion of said mechanical linkage.

13. The welding helmet of claim 12 wherein said mechanical linkage comprises a protrusion and slot, one of said protrusion and slot being located on said conical pivot stop and the other of said protrusion and slot being located on said strap member.

14. A welding helmet comprising at least one connector assembly joining a shell portion of the helmet to a head gear portion of the helmet, the connector assembly having first and second conical bearing surfaces engaged with each other to allow pivotal motion between the head gear portion of the helmet and the shell portion of the helmet about an axis, the connector assembly comprising a pivot stop member having a mechanical stop for limiting the pivotal motion between the head gear portion of the helmet and the shell portion of the helmet about the axis, the pivot stop member being secured to the shell of the helmet in a manner allowing the pivot stop member to be rotationally fixed in one of a plurality of orientations about the axis relative to the shell portion, the plurality of orientations allowing angular adjustment of the mechanical stop about the axis relative to the shell of the helmet.

15. The welding helmet of claim 14 wherein the pivot stop member is a monolithic part.

16. The welding helmet of claim 14 wherein the first conical bearing surface is formed on the pivot stop member.

17. The welding helmet of claim 14 wherein the mechanical stop is comprised of an arcuate groove formed in the pivot stop member, the head gear portion of the helmet has a protrusion that extends into the groove, and the groove has opposite circumferential ends configured and adapted to limit the pivotal motion between the head gear portion of the helmet and the shell portion of the helmet by engaging with the protrusion of the head gear portion of the helmet extending in to the groove.

18. The welding helmet of claim 14 wherein the shell portion of the helmet has a plurality of holes adjacent the axis and the pivot stop member has a protrusion radially offset from the axis that engages with one of the plurality of holes in the shell portion of the helmet to rotationally fix the pivot stop member in one of the plurality of orientations about the axis relative to the shell portion of the helmet.

19. The welding helmet of claim 14 further comprising an axial fastener for urging the head gear portion, the pivot stop member, and the shell portion together.

20. The welding helmet of claim 19 where in the fastener is axially adjustable and adjustment of the fastener adjusts the friction between the first and second conical surfaces to thereby adjust the ease of pivoting movement between the shell portion of the helmet and the head gear portion of the helmet.

* * * * *